US006328741B1

(12) United States Patent
Richelsoph

(10) Patent No.: US 6,328,741 B1
(45) Date of Patent: Dec. 11, 2001

(54) TRANSVERSE CONNECTOR

(75) Inventor: Marc Richelsoph, Memphis, TN (US)

(73) Assignee: Spinal Innovations, LLC, Bartlett, TN (US)

( * ) Notice: Subject to any disclaimer, the term of this patent is extended or adjusted under 35 U.S.C. 154(b) by 0 days.

(21) Appl. No.: 09/439,822

(22) Filed: Nov. 12, 1999

Related U.S. Application Data

(62) Division of application No. 08/735,072, filed on Oct. 18, 1996, now Pat. No. 6,171,311.

(51) Int. Cl.[7] .................................................. A61B 17/56
(52) U.S. Cl. ................................................. 606/61; 606/72
(58) Field of Search .................................. 606/61, 72, 73, 606/60; 623/17.11

(56) References Cited

U.S. PATENT DOCUMENTS

| 5,312,405 | * | 5/1994 | Korotko et al. | 606/61 |
| 5,662,651 | * | 9/1997 | Tornier et al. | 606/60 |
| 6,113,600 | * | 9/2000 | Drummond et al. | 606/61 |
| 6,171,311 | * | 1/2001 | Richelsoph | 606/61 |

* cited by examiner

Primary Examiner—David O. Reip
Assistant Examiner—Julian W. Woo
(74) Attorney, Agent, or Firm—Kohn & Associates

(57) ABSTRACT

A transverse connector includes a pair of transverse connector bodies and connector inserts for connecting a rod to each of the transverse connector bodies. A locking and fixing mechanism draws the transverse connector inserts into seat portions of the transverse connector bodies while simultaneously locking the transverse connector inserts in the insert seat portions and compressing a rod seat surface of the inserts to lock a rod within the rod seats. An interconnecting mechanism interconnects the pair of transverse connector bodies along an axis defined by the length of the transverse connector bodies.

3 Claims, 2 Drawing Sheets

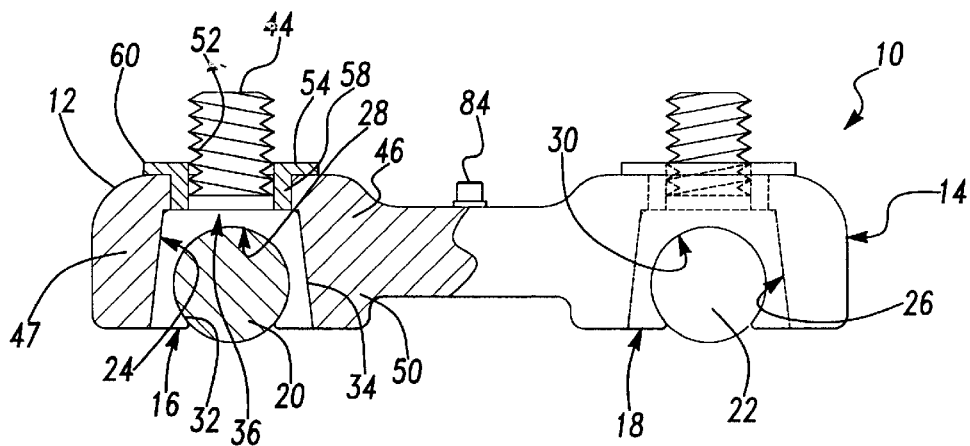
Fig-1
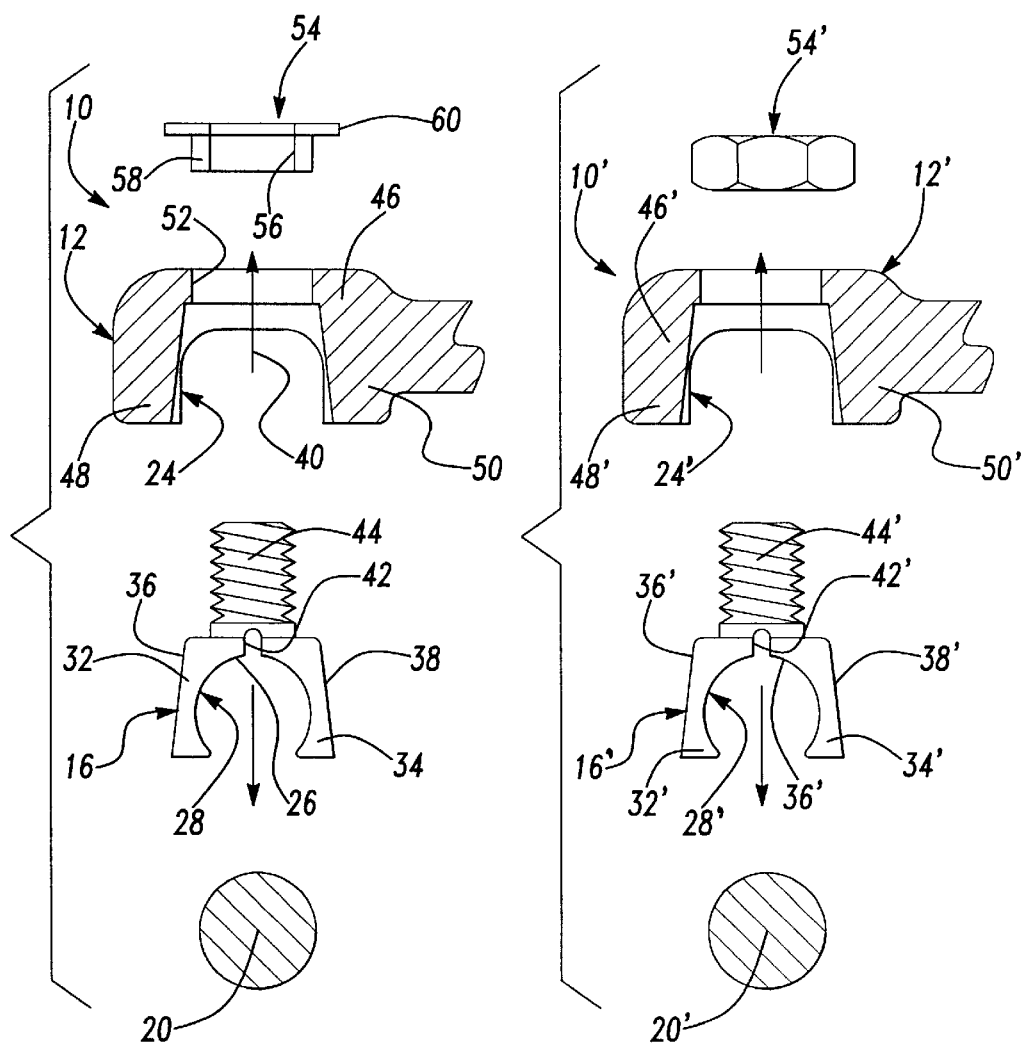
Fig-2
Fig-3

TRANSVERSE CONNECTOR

CROSS REFERENCE TO RELATED APPLICATIONS

This application is a divisional of U.S. patent application Ser. No. 08/735,072, filed Oct. 18, 1996 now U.S. Pat. No. 6,171,311.

TECHNICAL FIELD

The present invention relates to transverse connectors which generally include a pair of coupler bodies, each of the coupler bodies including a connecting mechanism for connecting each coupler body to a spinal rod for the purpose of interconnecting a pair of spinal rods. The present invention is a surgical tool or medical construct used with spinal rods for the purpose of spinal fixation and correction of spinal curve.

BACKGROUND OF THE INVENTION

Spinal rods are often used for spinal fixation, often times for correction of scoliotic curves. Fixation using such rods often involves implantation of rods and attaching them to the spine by hooks and/or screws. Usually, a pair of rods are placed on opposite sides of the portion of the spine to be fixed.

Various systems have been developed for cross linking spinal rods to prevent rod migration and to increase stiffness of the paired rod assembly.

Many assemblies used for interconnecting spinal rods, commonly referred to as transverse connector assemblies or rod to rod couplers, utilize a plate mechanism having openings therethrough for adjustably retaining hook systems that are bolted in place in the plate. Examples of such systems are in the U.S. Pat. No. 5,334,203 to Wagner, issued Aug. 2, 1994 and U.S. Pat. No. 5,522,816 to Dinello et al., issued Jun. 4, 1996. The U.S. Pat. No. 5,498,263 to Dinello et al., issued Mar. 12, 1996 discloses a transverse connector system utilizing set screws to interconnect vertebrae coupling members while also using plate members as described above for interconnecting the coupling members such that a squared unit is formed having two sides defined by the plate members and two sides defined by the spaced rod members.

The U.S. Pat. No. 5,312,405 to Korotko et al., issued May 17, 1995 discloses a coupler used for interconnecting spinal rods wherein the coupler itself is a two piece unit, the neck portion of each unit being interconnected by a screw mechanism which clamps a male portion within a female portion of the system. The system also utilizes coupler inserts or yokes which engage a rod and are compressed about the rod when disposed within a seat portion of each coupler and compressed by an instrument which engages the bottom of the rod between the rod and the spine and the top of the coupler.

It would be desirable to provide a coupler which could engage a rod by a simple locking mechanism. It is also desirable to provide a simple interconnecting mechanism between couplers which would require few parts and little manipulation to provide the interconnection. Further, it is desirable to provide a transverse coupler assembly which requires only a simple screw driver or nut driver outside of the assembly for its interconnection between a pair of spinal rods.

SUMMARY OF THE INVENTION

In accordance with the present invention there is provided a coupler for connection to a spinal rod, the coupler including a transverse connector body including insert seat means for seating a transverse connector insert therein and a transverse connector insert including rod seat means for seating a rod therein. Locking and fixing means draw the transverse connector insert into the insert seat means while simultaneously locking the transverse connector insert in the insert seat means and compressing the rod seat means to lock a rod within the rod seat means.

The present invention further provide a transverse connector comprising a pair of transverse connector bodies including connector means for connecting a rod to each of the transverse connector bodies and interconnecting means for interconnecting the pair of transverse connector bodies along an axis defined by the interconnecting means. The interconnecting means includes length locking means for locking the transverse connector bodies at a predetermined one of a plurality of distances apart along the axis and rotation locking means for preventing relative rotation about the axis between the transverse connector bodies.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a side view, partially in cross section of a transverse connector made in accordance with the present invention;

FIG. 2 is an exploded view, partially in cross section of a coupler made in accordance with the present invention;

FIG. 3 is an exploded view of a second embodiment of the inventive coupler;

DETAILED DESCRIPTION OF THE INVENTION

Figure 4:
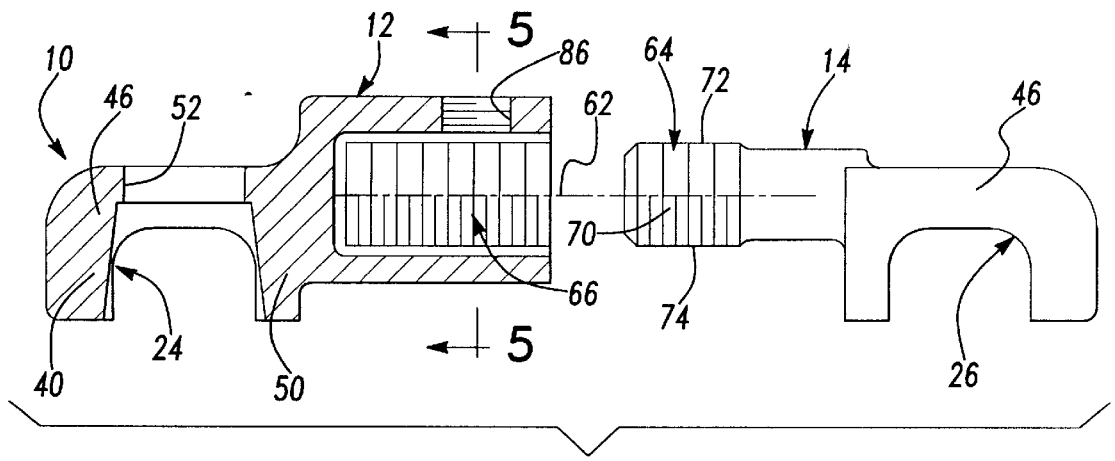
FIG. 4 is an exploded view of the transverse connector, partially in cross section.

A transverse connector constructed in accordance with the present invention is generally shown at 10 in its assembled condition in FIG. 1 and in an exploded view in FIG. 2.

Most generally, the connector 10 includes a pair of connector bodies generally shown at 12,14. Each transverse connector body 12,14 is associated with a connector insert 16,18 for connecting a rod 20,22 to each of the transverse connector bodies 12,14. A locking and fixing mechanism is provided for drawing the transverse connector inserts 16,18 into a seat portion 24,26 and while also simultaneously locking the insert 16,18 in the respective seat portion 24,26 while compressing a rod seat portion 28,30 of each insert 16,18 to lock a rod 20 within the rod seat portion 28,30.

More specifically referring to the transverse connector insert 16, the insert 16 includes a substantially U-shaped portion defined by side walls 32,34 and a base wall 36 combining to form a substantially arcuate inner surface thereof. The arcuate inner surface defines a rod seat surface for retaining a rod 20 therein. The arms 32,34 each have an outer surface 36,38, as best shown in FIG. 2, which taper or flare outwardly from a central axis 40 defined by the length of the insert member 16 when the insert member 16 is not disposed within the seat 24 of the coupler 12. A groove 42 extends through the base portion 26 of the insert 16, the groove 42 extending perpendicular to the axis 40. The groove allows for flexibility of inward motion of the arms 32,34 with the insert 16 as seated within the seat 24, as described below in more detail.

The insert 16 also includes a connector portion extending therefrom along the axis 40. The connector portion is shown in the Figures to be a threaded shaft 44. Although other configurations of the connector portion 44 can be made by those skilled in the art, the preferred embodiment includes the threaded portion for reasons set forth in detail below.

Referring specifically to FIG. 2, the transverse connector body 12 is substantially U-shaped when viewed in cross section. The transverse connector body 12 includes a base portion 46 and a pair of arms 48,50 defining the U-shaped cross section. The inner surface of the arms 48,50 and base portion 46 define the insert seat surface 24,26. Preferably, the inner surface of the arm portions 48,50 taper outwardly. That is, the seating surface is wider at its distal end than at its surface defined by the base portion 46. The outward taper is designed to be at an extent less than the outward taper of the outer surfaces 36,38 of the insert member 16.

The base portion 46 of the transverse connector body 12,14 includes an opening 52 extending therethrough. The opening 52 extends completely from the seating surface 24 through to the outer surface of the insert 16. That is, it extends complete through the base portion 46.

The locking mechanism of the invention preferably includes a nut member generally shown at 54 in FIGS. 1 and 2. The nut member 54 is adapted to engage a distal end of the threaded connector portion 44 as the substantially U-shaped portion of the insert member 16 defined by the legs 32,34 and seat portion 26, is seated and compressed within the insert seat 28. The connector portion 44 extends through the opening 52.

As best shown in FIG. 1, the nut member 54 engages and locks the insert 16 within the insert seat 24.

More specifically, the member 54 includes an inner threaded surface 56 which threadedly engages the outer threaded surface 44 of the connector portion 44. As the nut member 54 is threaded onto the threaded connector portion 44, the substantially U-shaped portion of the insert member 16 is drawn into the seating surface 24. If a rod 20 is disposed within the seat 28 of the insert 16, the arms 32,34 are compressed about and into an engagement with the rod 20 as the arms 32,34 deflected inwardly by the ordinarily spaced inner surfaces of the arms 48,50 of the transverse connector body 12,14. Thusly, the locking of the insert 16 simultaneously fixes the rod 20 within the assembly 10. That is, a single locking action of the nut member 54 to the threaded connector 44 simultaneously connects the insert 16 to the transverse connector body 12 while also fixing the rod 20 to the transverse connector 10. In other words, a single connection fixes the rod 20 and insert 16 to the assembly 10. The transverse connector is shown in the assembled position in FIG.

The pair of arms 32, 34 and base portion 36 form a arcuate grooved surface, the groove defining a rod seat axis along the length thereof. The groove 42 extends between the arms 32,34 and parallel to the rod seat axis. The groove 42 allows for improved flexibility of the arms 32,34 as they are deflected during the seating action of the insert 16 into the seating surface 24. The groove 42 allows for easier inward deflection of the arms 32,34 while also allowing for complete deflection of the arms 32,34 as opposed to merely the more flexible portion of the arms 32,34. Thusly, the entire inner surface of the rod seat surface 28 grips the rod 20 during the inward compression of the arms 32,34 as the insert 16 is seated within the insert seat surface 24 of the transverse connector bodies 12,14.

Several alternative embodiments of the invention can be made. For example, the connector portion 44 can include a threaded internal passageway and the nut member 54 can include a stud portion extending therefrom and having an externally threaded surface for mating threaded engagement with the internal threaded passageway of the connector portion 44.

In a second embodiment, as shown in FIGS. 1 and 2, the nut member 54 includes a neck portion 58, the neck portion 58 including the internal threaded portion 56. The nut member 54 also includes a radially outwardly extending flange 60, preferably at a distal end thereof. The opening 52 of the transverse connector body 12 seats the neck portion 58 of the nut member 54 therein, as shown in FIG. 1 when the nut member 54 threadedly engages the connector portion 44. The flange 60 provides a stop for engaging an outer surface of the transverse connector body 12. A further, more simpler embodiment of the present locking mechanism is shown in FIG. 3 wherein primed numerals are used to show like structure between the several embodiments. In this embodiment, a simple nut member 54' is disposed over the threaded shaft 44' of the insert member 16'. This embodiment does not have the lower profile of the nut member 54 shown in FIGS. 1 and 2 operates in the same manner.

Figure 6:
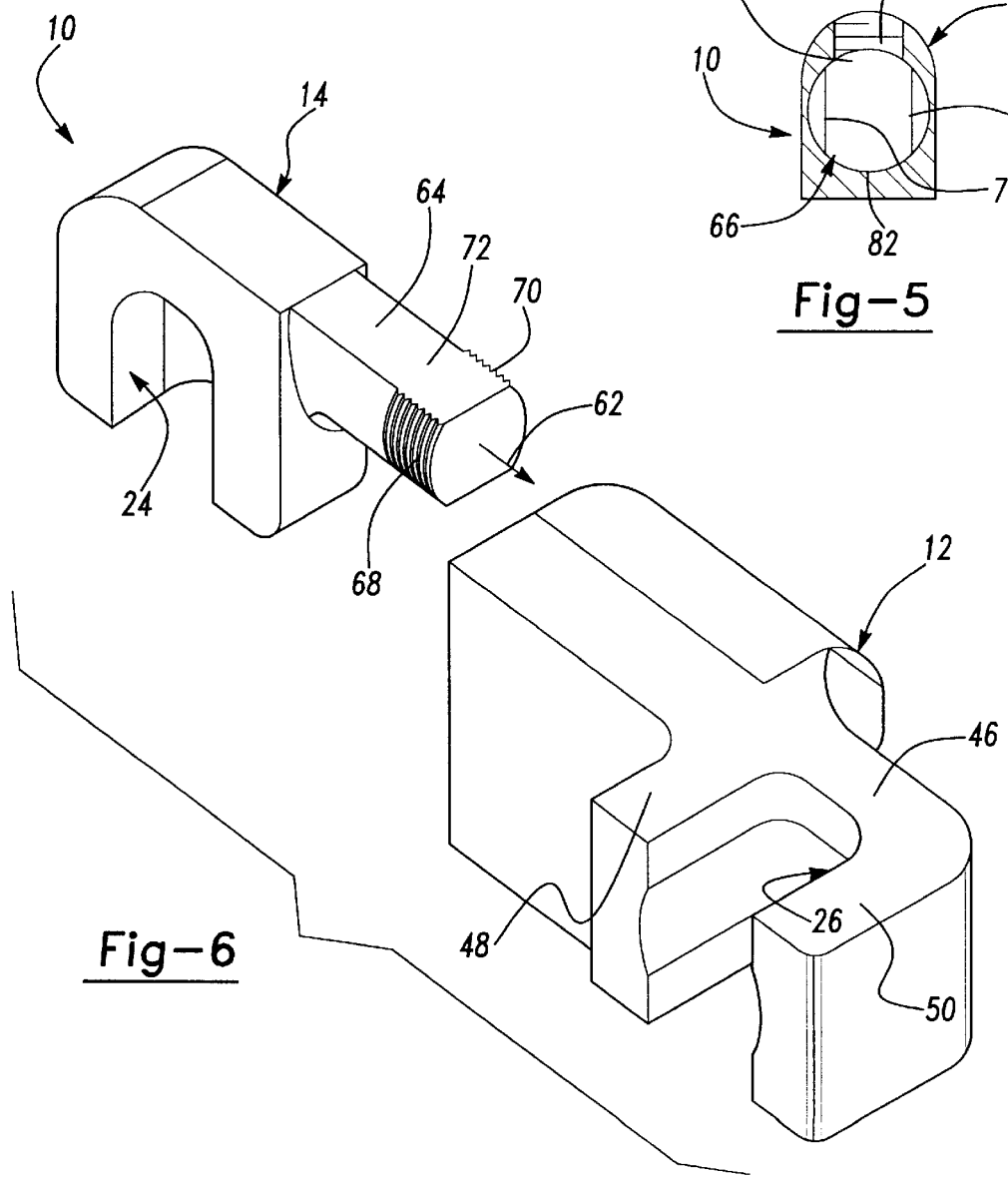
FIG. 6 is an exploded view of the transverse connector in a presassembled position.

As shown in FIGS. 1, 4 and 6, the preferred embodiment of the present invention includes a pair of transverse connector bodies 12,14. The bodies 12,14 have structural entities which combine to interconnect the pair of transverse connector bodies 12,14 into a single unitary transfer connector unit. The interconnection is completed by a length locking mechanism which locks the transverse connector bodies 12,14 at a predetermined one of a plurality of distances apart along an axis shown in FIG. 4 at 62 defined by the length of the length locking mechanisms. The transverse connector 10 further includes a mechanism for locking relative rotation between the bodies 12, 14 at a desired joined position of the bodies 12,14.

More specifically, and referring to FIGS. 4 and 6, the length locking mechanism includes a male portion generally shown at 64 extending from one of the transverse connector bodies 14 and a female portion 66 within the other transverse body portions 12. The length locking mechanism includes a pair of threaded portions 68,70, as best shown in FIG. 6. The threaded portions 68,70 are separated by flat relieved portions 72,74, as best shown in FIG. 4. The female portion 66 includes internal threaded portions 76,78 and recessed or machined flat portions 80,82 therebetween. The threaded and flat portions 76,78, 80, 82 are symmetric with the threaded and flat portions 68,70,72,74 of the male portion 64.

Figure 5:
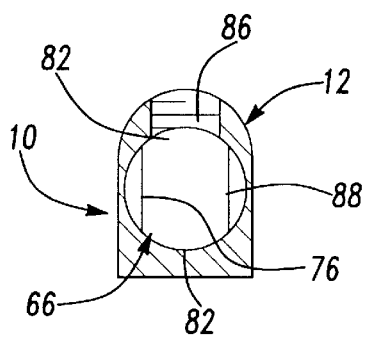
FIG. 5 is a cross section taken substantially along lines 5—5 of FIG. 4.

FIG. 5 shows a cross-section view of the female portion illustrating the oppositely facing threaded portions 76,78 and the recessed or flat portions 80,82. The term "flat portion" is used to mean an unthreaded portion or portion where threads have been machined away. This portion must provide a sufficient recessed area to allow insertion of the male portion 64 with the threaded portion 68,70 sliding past the recessed flat portions 80,82 without contact or at least without frictional engagement. Thus, the flat portions 80,82 can be somewhat arcuate in shape, as shown in FIG. 5 or substantially flat but in either event must provide access and clearance for the threaded portions 68,70 and the male portions 60 to be insert therethrough. In other words, the flat portions 80,82 of the female portion 66 is recessed for allowing sliding mating seating of the male portion 64 into the female portion 66 without engagement of the threaded male portions 68,70 with the flat portions 80,82 of the female portion 66. However, the threaded portions 76,78 of the female portion 66 are spaced for threaded engagement with the threaded male portions 68,70 so that rotation of the male portion 64 relative to the female portion 66 engages and disengages the threaded portions 68,70 of the male portion 66 from the threaded portion 76,78 of the female portion 66. Thus, the locking mechanism includes a first position, as shown in FIG. 6 of the transverse connector bodies 12,14 relative to each other allowing distance adjustment between the transverse connector bodies 12,14 axially along the axis 62. In this first position, the seating surfaces 24,26 are offset 900 while the threaded surfaces 68,70 of the male portion 64 align with the recessed flat portions 80,82 of the female portion 66. Likewise, the flat portions 72,74 of the male portion 64 are in alignment with the threaded portions 76,78 of the female portions 66. The flat portions 72,74 are machined so as to also pass without frictional engagement by the threaded portions 76,78 of the female portion. The transverse connector bodies 12,14 may be rotated 90° along the axis 62 into a second position as shown in FIG. 1. In this positioning, the transverse connector bodies 12,14 are rotated about the axis 62 into a locked condition with regard to the connector bodies 12,14 moving closer or farther apart along the axis 62. The locking action is effected by the engagement of the threads 68,70 of the male portion being brought into threaded engagement with the threads 76,78 of the female portion as a result of the 900 turn from the first position to the second position. In the second position, the threads catch, providing solid holding from linear movement along axis 62 of the male portion 64 relative to the female portion 66.

To maintain this second position, rotation of the transverse connector bodies 12, 14 relative to each other must be prevented. Hence, a rotation locking mechanism is provided. The rotation locking mechanism includes a locking member, preferably in the form of a lock screw 84, shown in FIG. 1. The lock screw 84 is disposed through a threaded opening 86 in the female portion 66, as shown in FIGS. 4 and 5. The set screw 84 extends into at least one of the flat portions 82 of the female portion 66 for engaging a flat surface 72 of the male portions 68,70 for preventing rotation thereof and fixing the threaded male portion 64 in threaded engagement with the threaded female portions 76,78 thereby fixing and locking the distance between the transverse connector bodies 12,14.

In use, the rod members 20,22 would be fixed to the spine by means well known in the art to surgeons specializing in the art. The interconnecting of the rods 20,22 can be perfected by a variety of sequenced events utilizing the present invention. For example, a first connector insert 16 can be disposed on rod 20. The insert 16 can have an arcuate outer surface to allow for the seating surface 24 to be dispose thereover in a range of positions relative to the axis defined by the rod 20. A range of motion is between −15° 15° and relative to a perpendicular relationship between the axis 62 defined by the length of the connector 10 and the axis defined by the rod 20. This angulation can be easily increased or decreased and is not limited to any angulation. The insert 16 is then drawn into the seat portion 24 of the transverse connector body 12 by the threading of the nut member 54 onto the connector portion 44. The second insert 18 is then disposed on rod 22 and inserted through the opening 52 in the transverse connector body 14 and the nut member 54 is threadedly connected to the threaded connector portion 44 thereby completing the inner connection of the rods 20,22.

During the connection, once the first rod is connected to the transverse connector body 12, the male portion 64 of the other transverse connector body 14 is inserted into the female portion 66 until the desired distance between the transverse connector bodies 12,14 is achieved. The transverse connector body 14 is then rotated 90° to engage the threaded portions 68,70 thereof with the threaded portions 76,78 of the female portion 66 to lock the distance between the transverse connector bodies 12,14. The set screw 84 is then inserted into the threaded opening 86 to prevent relative rotation between the connector bodies 12,14 and fixed their length. As stated above, the sequence of events can be altered to achieve the same results.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

What is claimed:

1. A transverse connector (10) comprising a pair of transverse connector bodies (12,14) including connector means (16,18) for connecting a rod (20,22) to each of said transverse connector bodies (12,14) and interconnecting means for interconnecting said pair of transverse connector bodies (12,14) along an axis (62) defined by said interconnection means comprises length locking means for locking said transverse connector bodies (12,14) at a predetermined one of a plurality of distances apart along axis (62) defined by said length locking means and rotation locking means for preventing relative rotation about said axis between said transverse connector bodies (12,14), said length locking means including a male portion (64) extending from one of said transverse connector bodies (14) and a female portion (66) within the other of said transverse body portions (12), said locking means including a pair of threaded portions (68,70) on said male portion (64) separated by flat portions (72,74) and said female portion (66) including threaded (76,78) and flat portions (80,82) symmetric with said threaded and flat portions (68,70,72,74) of said male portion (64), said flat portions (80,82) of said female portion (66) being recessed for allowing sliding mating seating of said male portion (64) into said female portion (66) without engagement of said threaded male portions (68,70) with said flat portions (80,82) of said female portion (66), said threaded portions (76,78) of said female portion (68) being spaced for threaded engagement with said threaded male portions (68,70) so that rotation of said male portion (64) relative to said female portion (66) engages and disengages said threaded portions.

2. A transverse connector (10) as set forth in claim 1 wherein said female portion includes a set screw (84) extending into at least one of said flat portions (82) thereof for engaging a flat surface (72) of said male portion (64) preventing rotation thereof and fixing said threaded male portion (64) in threaded engagement with said threaded female portions (76,78) thereby fixing and locking the distance between said transverse connector bodies (12,14).

3. A coupler for connection to a spinal rod (20), said coupler comprising: a transverse connector body (12,14)

including a pair of insert seat means (24,26) for seating transverse connector inserts (16,18) therein; wherein each transverse connector insert (16,18) includes rod seat means (28,30) for seating a rod (20) therein, said transverse connector insert (16,18) further includes a pair of arms (32,34) defining a rod seat axis therebetween along which a rod (20) is seated said rod seat means (28) including a groove (42) extending between said arms (32,34) and parallel to said rod seat axis; and locking and fixing means for drawing a transverse connector insert (16,18) into each of said insert seat means (24,26) while simultaneously locking said transverse connector insert (16,18) in each of said insert seat means (24,26) and compressing said rod seat means (28,30) to lock a rod (20) within said rod seat means (28,30).

\* \* \* \* \*